United States Patent
Huang et al.

(10) Patent No.: US 11,912,973 B2
(45) Date of Patent: Feb. 27, 2024

(54) FACILITATING CELL GROWTH USING A DYNAMIC SCAFFOLD

(71) Applicant: Ark Biotech Inc., Westwood, MA (US)

(72) Inventors: Zheng Huang, Bolton, MA (US); Orianna Elysse Kane, Boston, MA (US); Xiaoting Liang, Columbus, OH (US); Natalie Rose Rubio, Malden, MA (US)

(73) Assignee: Ark Biotech Inc., Westwood, MA (US)

( * ) Notice: Subject to any disclaimer, the term of this patent is extended or adjusted under 35 U.S.C. 154(b) by 0 days.

(21) Appl. No.: 18/204,603

(22) Filed: Jun. 1, 2023

(65) Prior Publication Data

US 2024/0034977 A1 Feb. 1, 2024

Related U.S. Application Data

(60) Provisional application No. 63/392,612, filed on Jul. 27, 2022.

(51) Int. Cl.
  C12M 1/12 (2006.01)
  C12M 1/00 (2006.01)
  C12M 1/34 (2006.01)

(52) U.S. Cl.
  CPC ........... C12M 25/14 (2013.01); C12M 23/40 (2013.01); C12M 41/44 (2013.01)

(58) Field of Classification Search
  CPC ....... C12M 25/14; C12M 23/40; C12M 41/44
  USPC .................................................... 435/289.1
  See application file for complete search history.

(56) References Cited

U.S. PATENT DOCUMENTS

| | | | |
|---|---|---|---|
| 8,492,135 B2* | 7/2013 | Porter | C12N 5/0068 435/325 |
| 2006/0019388 A1* | 1/2006 | Hutmacher | C12M 41/32 435/298.2 |
| 2007/0286880 A1* | 12/2007 | Vasiliev | A61L 27/3813 435/395 |
| 2014/0273222 A1* | 9/2014 | Weinberger | C12N 5/0062 435/395 |
| 2015/0064142 A1* | 3/2015 | Green | A61L 27/56 623/23.72 |
| 2020/0024560 A1* | 1/2020 | Zhang | C12M 29/10 |

OTHER PUBLICATIONS

Author Unknown, Tension Cell Stretching Bioreactor System, Flexcell International, May 21, 2023.

* cited by examiner

*Primary Examiner* — Michael L Hobbs
*Assistant Examiner* — Lenora A Abel
(74) *Attorney, Agent, or Firm* — Van Pelt, Yi & James LLP

(57) ABSTRACT

A bioreactor includes a scaffold, a scaffold support, and a manifold. The scaffold is seeded with a plurality of cells. The scaffold has an extended state and a non-extended state. The scaffold support that selectively modifies a state of the scaffold from the non-extended state to the extended state. A manifold is configured to provide a medium to the scaffold. The state of the scaffold from the non-extended state to the extended state is modified at a rate tuned to maintain a cell density associated with the plurality of cells within a particular density range.

23 Claims, 15 Drawing Sheets

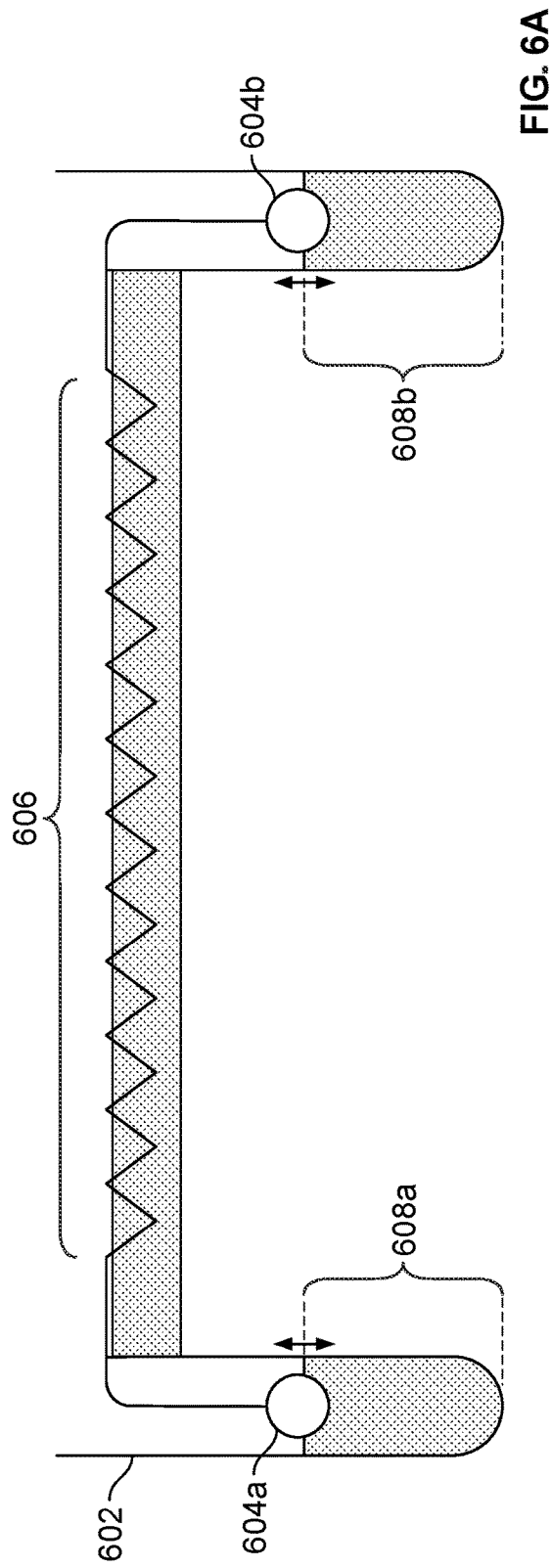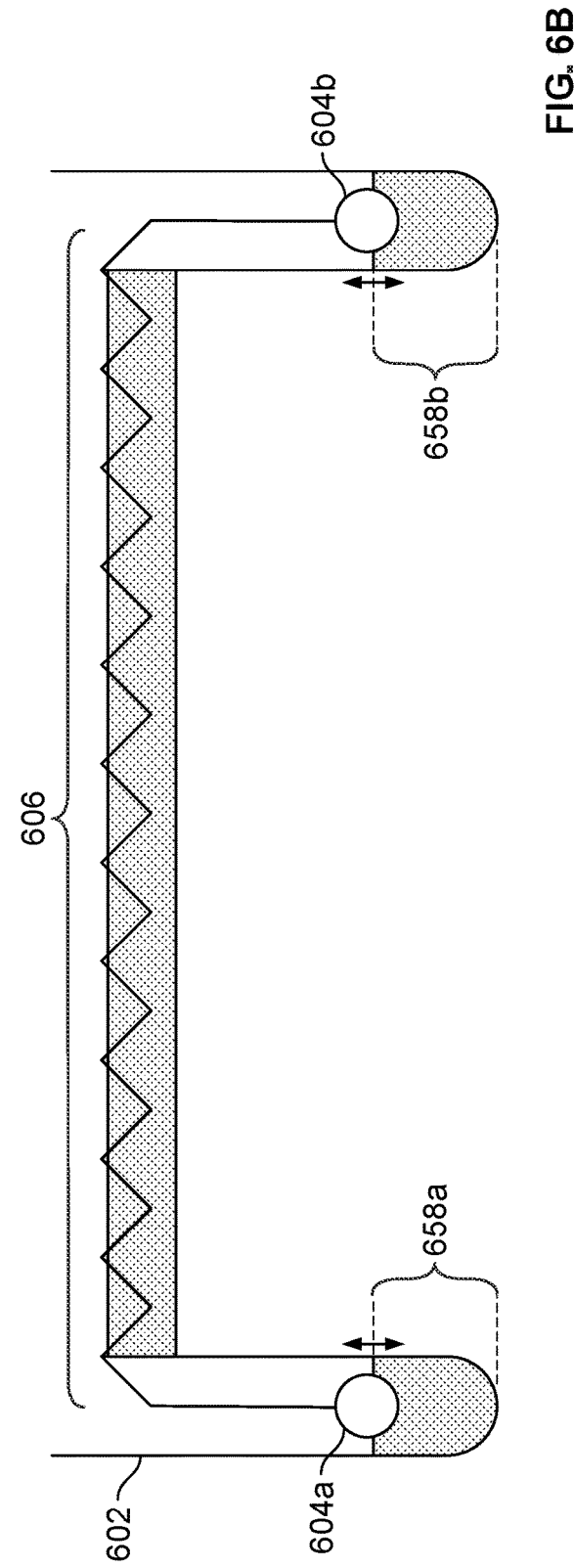

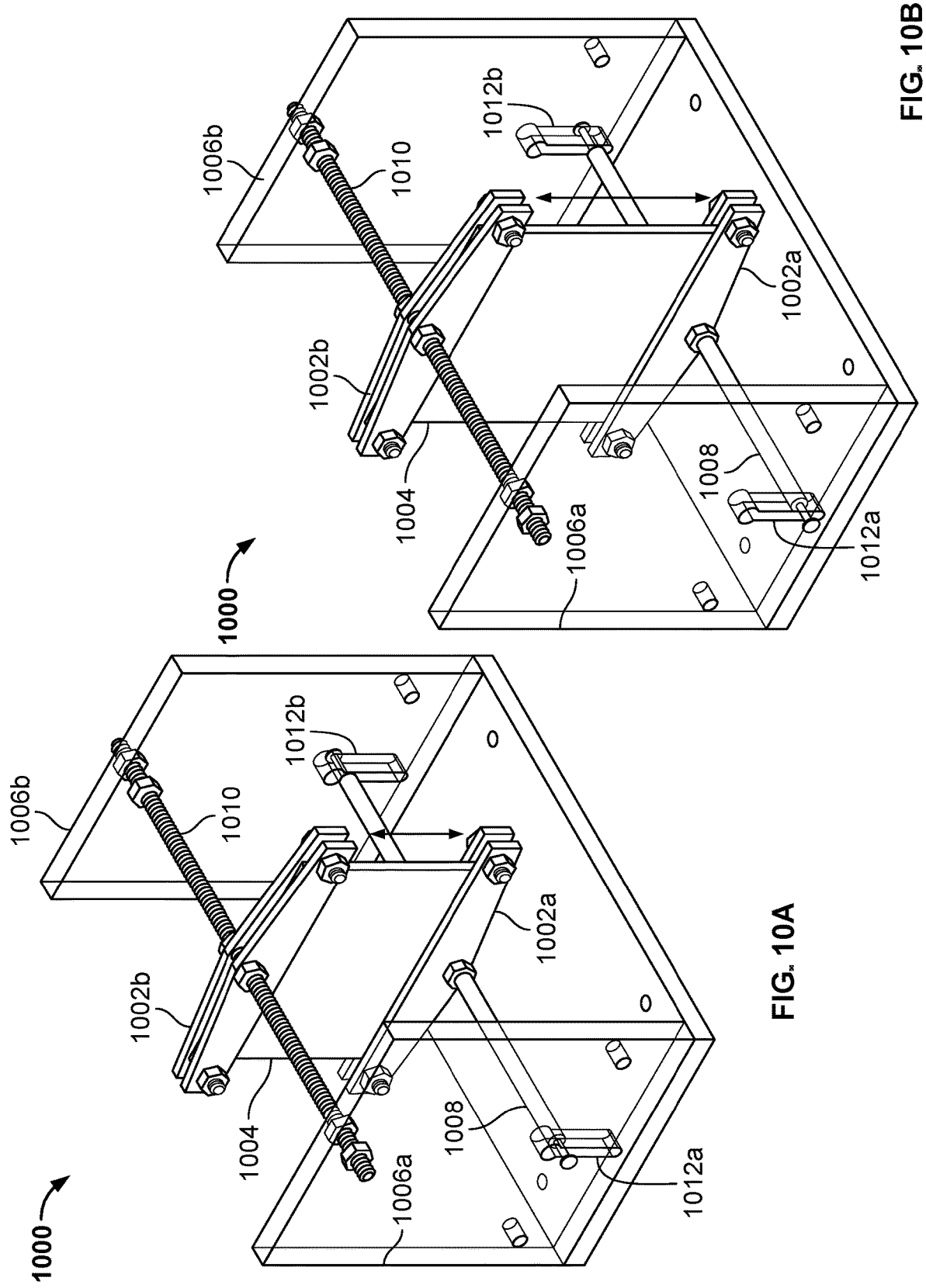

FACILITATING CELL GROWTH USING A DYNAMIC SCAFFOLD

CROSS REFERENCE TO OTHER APPLICATIONS

This application claims priority to U.S. Provisional Patent Application No. 63/392,612 entitled DYNAMIC SCAFFOLD DESIGN filed Jul. 27, 2022 which is incorporated herein by reference for all purposes.

BACKGROUND OF THE INVENTION

Scaffolds are materials to which cells adhere during proliferation and/or differentiation. For cultured meat applications, scaffolds provide surface area, surface cues, and structure to developing tissues and can influence end-product characteristics (e.g., cell phenotype, organoleptic properties, nutritional profile). Current approaches for scaffold seeding and culture involve pre-fabricating a porous scaffold, adding a cell suspension to the scaffold under static conditions, and allowing the cells to adhere, migrate, proliferate, and differentiate within the scaffold. Differentiation cues include scaffold topography, medium components, or the application of electrical, mechanical, or chemical stimuli. Challenges facing scaffold development include achieving bulk infiltration during cell inoculation and producing a targeted tissue structure. Due to insufficient cell migration as well as nutrient and oxygen diffusion limitations, cells seeded within scaffolds often adhere to the outer edges of the scaffold and do not infiltrate the bulk of the material. Many reported attempts fail to penetrate beyond the first ~2 mm depth and to synthesize correct muscle fiber formation, thus do not meet the market expectation for structured meat products. To grow "whole-cut" meat products, cells should be evenly distributed throughout the bulk of the scaffold material. To improve cell-scaffold systems for cultured meat production, the entire construct should be the size, thickness, and shape of the target meat product and cultured muscle fibers should be aligned macroscopically.

BRIEF DESCRIPTION OF THE DRAWINGS

Various embodiments of the invention are disclosed in the following detailed description and the accompanying drawings.

FIG. 6A is a diagram illustrating a scaffold support in a vessel in accordance with some embodiments.

FIG. 6B is a diagram illustrating a scaffold support in a vessel in accordance with some embodiments.

FIGS. 10A and 10B are diagrams illustrating a scaffold support in accordance with some embodiments.

DETAILED DESCRIPTION

Figure 1A:
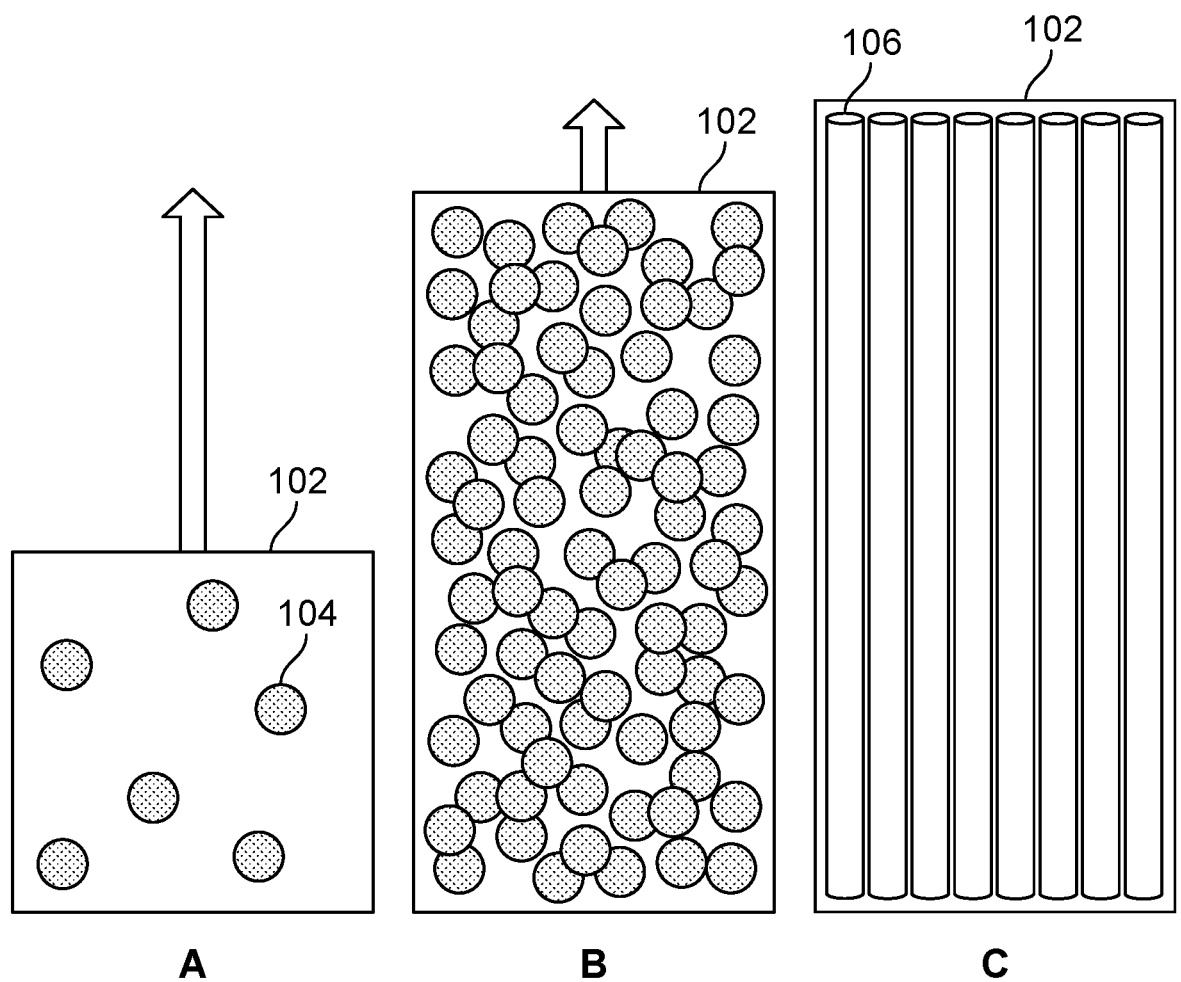
FIG. 1A is a diagram illustrating a process of expanding a scaffold and inducing cell differentiation in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A dynamic scaffold system designed to facilitate cultured meat cells to adhere, migrate, proliferate, and/or differentiate within scaffold materials is disclosed herein. In some embodiments, the dynamic scaffold system is utilized in a bioreactor. In some embodiments, the dynamic scaffold system is utilized in a fermenter. Utilizing the disclosed dynamic scaffold, cells can distribute uniformly and align unidirectionally to better approximate natural muscle. In contrast with current methods, the disclosed dynamic scaffold offers benefits of improved cell distribution, dynamic surface area for extended proliferation, and cell alignment for myogenic differentiation.

Cell Seeding

Cells are initially seeded within a thin, compact scaffold. The dimensions of the scaffold can be tuned to match the infiltration depth of the specific cell type and scaffold material combination. For example, if through initial research, a particular cell type is found to be able to migrate up to 2 mm within a scaffold of material composition and structure, the initial thickness of the scaffold can be tuned to 2 mm. In some embodiments, the cells are mammalian, avian, fish, reptile, crustacean, or Mollusca cells. In some embodiments, the cells are plant cells. In some embodiments, the cells are rodent, primate, or insect cells.

Figure 1B:
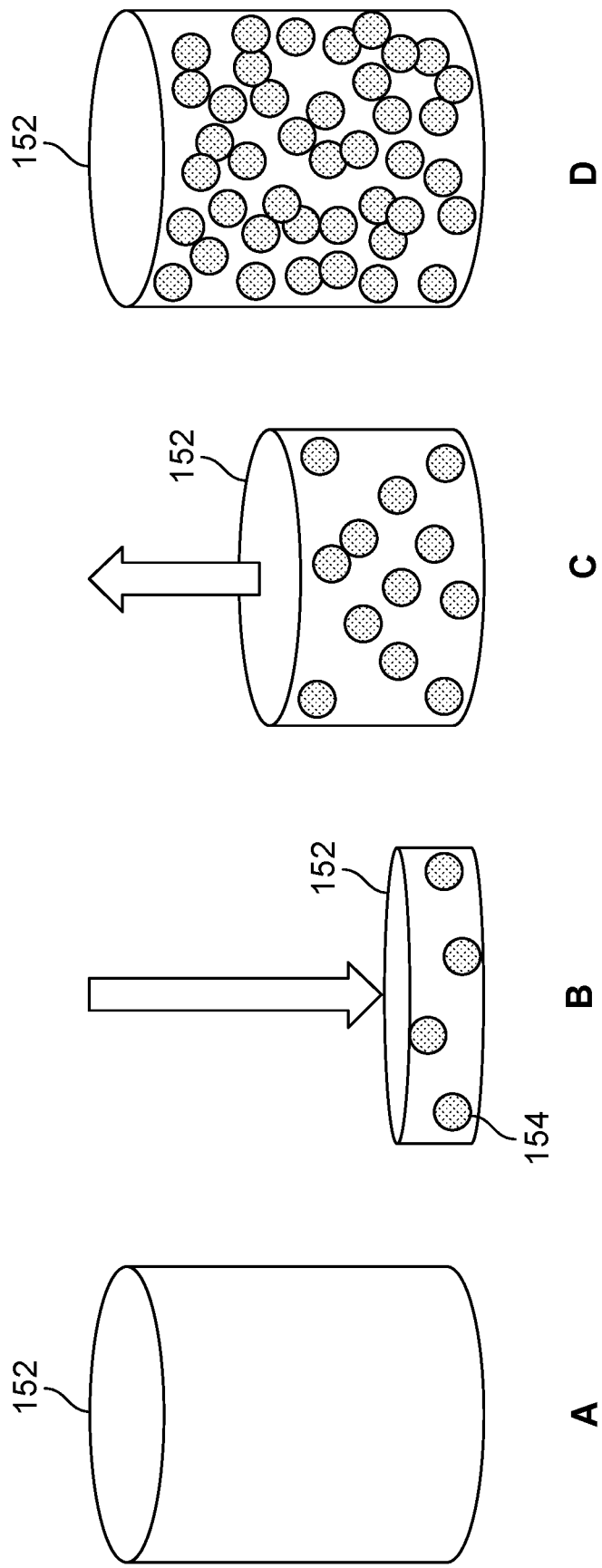
FIG. 1B is a diagram illustrating a process of expanding a scaffold and inducing cell differentiation in accordance with some embodiments.
Figure 1C:
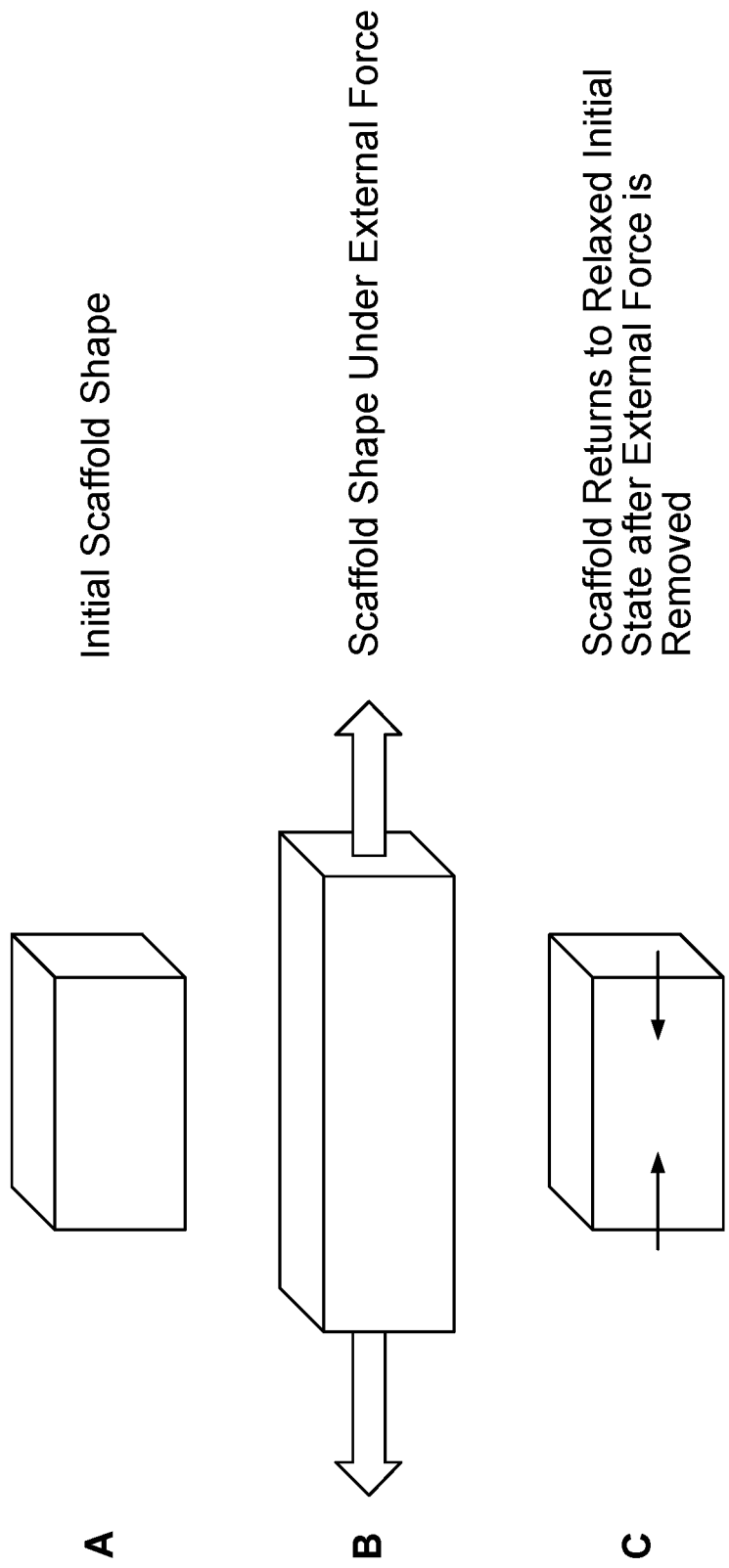
FIG. 1C is a diagram illustrating an example of a shape-memory scaffold in accordance with some embodiments.

To create the target scaffold thickness, in various embodiments, (a) a non-elastic scaffold can be compressed, (b) an elastic scaffold can be sectioned to the appropriate size, or (c) a shape-memory scaffold can be used (as seen in FIG. 1C). In the case of a non-elastic scaffold, the compaction may increase the density of the scaffold material or create micro-folds that will be inaccessible to cells. However, given the limited dimension of the scaffold, the cells can migrate through the entire depth of the material and adhere at numerous points. In the case of an elastic scaffold, the default or static state of the scaffold will be the state at which seeding occurs and compaction is not necessary.

Once all seeded cells have adhered to the scaffold, the scaffold can be decompressed (non-elastic scaffolds) or stretched (elastic scaffolds) for the cell proliferation phase. This will help cells to develop desired morphology.

Cell Proliferation

When adherent cells proliferate, they grow optimally within a density range. The minimum density limit is determined by necessary cell signaling requirements. For example, adherent cells seeded below 2,000 cells/cm2 may exhibit poor growth rates. A maximum density limit is determined by confluency. Due to the phenomenon of contact inhibition, when certain cell types make sufficient direct contact with other cells, they exit the cell cycle and begin to differentiate. Therefore, to encourage and extend the proliferation phase, the scaffold can be decompressed (non-elastic scaffolds) or stretched (elastic scaffolds) at a rate tuned to keep the cell density within the bounds of the desired density range. The size of the scaffold at a specific time, s(t), is equal to the total cell population on the scaffold at the specific time divided by the minimum seeding density, D_min.

The total cell population is calculated by:

$$N_o * e^{\frac{t*ln(2)}{dt}}$$

where $N_o$ is the initial population, t is time, and dt is the doubling time of the cell culture.

Therefore, $$s(t) = \frac{N_0 * e^{\frac{t*ln(2)}{dt}}}{D\_min}.$$

These equations may be used to determine how much to decompress or stretch the scaffold to keep the cell density within the bounds of the desired range.

Expanding the scaffold will continuously increase the surface area available to the cells, inhibiting contact inhibition and enabling a longer proliferation phase while maintaining the minimum cell density necessary to maintain optimal growth. Compared to static scaffold culture, dynamically expanding the scaffold will allow for lower cell inoculation densities and enable higher final cell densities.

In some embodiments, the scaffold is expanded until the maximum volume is achieved. In some embodiments, the scaffold is expanded by placing the scaffold on a surface and compressing a top portion of the scaffold. In some embodiments, the scaffold is expanded by placing the scaffold on a surface of a movable component and moving a bottom portion of the scaffold towards a fixed surface. In some embodiments, the scaffold is expanded by compressing a top and bottom portion of the scaffold in parallel. In some embodiments, the scaffold is expanded by holding a distal end of the scaffold at a fixed position and pulling a proximal end of the scaffold in a direction opposite of the distal end of the scaffold. In some embodiments, the scaffold is expanded by pulling both the distal end and the proximal end of the scaffold in opposite directions.

The maximum volume may be dictated by the mechanics of the scaffold or the target size of the end-product. The extent of expansion by the end of the cell proliferation phase may be intentionally reduced, so that the scaffold may be further expanded during the cell differentiation phase. At the final expansion volume, cells may continue to proliferate until a maximum or target density is achieved. Maximum cell density may be monitored via glucose (or other metabolites) consumption rate equilibrium. Cell density may also be monitored using sensor technology (e.g., capacitance, optical, etc.).

Cell Differentiation

After a maximum cell density is achieved during the cell proliferation phase, cell differentiation can be triggered. Differentiation can be induced by an alternate culture medium formulation and/or mechanical, electrical, or chemical stimuli. For example, differentiation of myogenic precursor cells may be induced by gradually transitioning media supplemented with a certain concentration of a set of growth factors to a disparate media source, supplemented with a different concentration of a different set of growth factors.

In some embodiments, differentiation is induced or enhanced by further expanding (e.g., decompressing, stretching) the scaffold. For myogenic cells, it has been shown that unidirectional tension induces myofiber alignment and enhanced differentiation. In some embodiments, scaffold expansion is the source of unidirectional tension. Compared to systems without tension applied, the disclosed system can result in a greater degree or rate of myogenic differentiation and/or myofiber alignment.

For myogenic differentiation, scaffold expansion and compaction could be cycled to simulate "exercise." This may result in further increased extent or rate of differentiation, due to the applied stress.

Scaffold Expansion

The scaffold can take a variety of forms, be composed of a variety of materials, and can be manipulated via a variety of methods.

Forms—Scaffolds could take the shape of films/membranes, fibers, fibrous sponges, porous sponges, or hydrogels. The scaffold may remain in the end-product, be detached from the tissue at some point in the bioprocess, prior to packaging, or be dissolved at some point in the bioprocess, prior to packaging.

Materials—Scaffolds could be composed of natural or synthetic materials that may or may not be post-processed or functionalized (e.g., conjugated with RGD motifs). Common materials may include extracellular matrix proteins or analogs, materials derived from non-animal sources (e.g., cellulose, chitosan, alginate, starch, silk) or recombinant peptides or proteins. Some materials may be reusable rather than edible or degradable and may require detachment from the cell culture during harvest. Detachment of tissue from scaffolds can be achieved via mechanical, enzymatic or other means.

Methods—Mechanical manipulation may occur via compression, decompression, stretching, or other means. The direction of expansion may be unidirectional or multidirectional. The material may be engineered to retain "shape-memory" and can alternate between multiple geometries based on external stimulus (e.g., temperature).

FIG. 1A is a diagram illustrating a process of expanding a scaffold and inducing cell differentiation in accordance with some embodiments. In the example shown, (A) depicts an initial non-extended state of scaffold 102. Scaffold 102 includes a plurality of cells, such as cell 104. The plurality of cells are seeded within scaffold 102. The dimensions of scaffold 102 can be tuned to match the infiltration depth of the specific cell type and scaffold material combination. Once all seeded cells have adhered to scaffold 102, scaffold 102 may be modified from the initial non-extended state to an extended state as seen in (B). The adherent cells proliferate when they grow optimally within a density range. Scaffold 102 may be stretched at a rate tuned to keep the cell density within the bounds of the desired density range. Expanding scaffold 102 will continuously increase the surface area available to the plurality of cells, inhibiting contact inhibition and enabling a longer proliferation phase while maintaining the minimum cell density necessary to maintain optimal growth. The increased surface area allows for extended proliferation. Cells proliferate until they reach maximum achievable density.

Differentiation can be triggered after maximum achievable cell density is reached. Differentiation may be induced by introducing scaffold 102 to an alternate culture medium formulation and/or mechanical, electrical, or chemical stimuli. For myogenic differentiation, as seen in (C), myocytes will fuse into myotubes, such as myotube 106 and develop into myofibers. Scaffold 104 can be expanded further to create tension. The tension induces myogenic cell alignment, resulting in parallel fibers.

FIG. 1B is a diagram illustrating a process of expanding a scaffold and inducing cell differentiation in accordance with some embodiments. In the example shown, (A) depicts an initial state of scaffold 152. As seen in (B), scaffold 152 is compressed into a non-extended state of scaffold 152. Scaffold 152 includes a plurality of cells, such as cell 154. The plurality of cells are seeded within scaffold 152. The degree to which scaffold 152 is compressed can be tuned to match the infiltration depth of the specific cell type and scaffold material combination. Once all seeded cells have adhered to scaffold 152, scaffold 152 may be modified from the non-extended state as seen in (B) to an extended state as seen in (C) and (D). The adherent cells proliferate when they grow optimally within a density range. Scaffold 152 may be decompressed at a rate tuned to keep the cell density within the bounds of the desired density range. Decompressing scaffold 152 will continuously increase the surface area available to the plurality of cells, inhibiting contact inhibition and enabling a longer proliferation phase while maintaining the minimum cell density necessary to maintain optimal growth. The increased surface area allows for extended proliferation. Cells proliferate until they reach maximum achievable density. After the maximum cell density has been reached, differentiation can be triggered to scaffold 152 in a similar manner as differentiation is triggered to scaffold 102.

Figure 2:
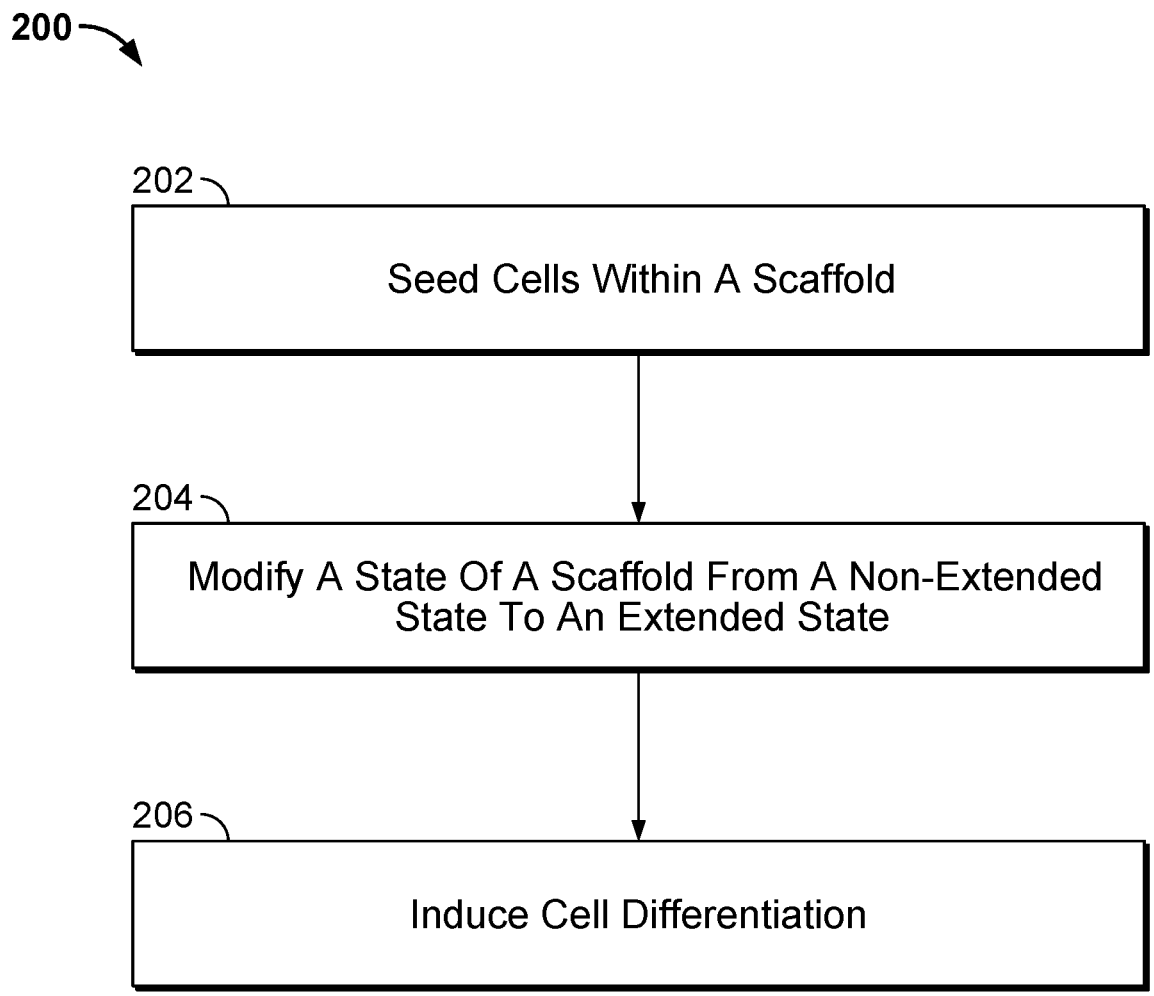
FIG. 2 is a flow diagram illustrating a process for growing "whole cut" meat products in accordance with some embodiments.

FIG. 2 is a flow diagram illustrating a process for growing "whole cut" meat products in accordance with some embodiments.

At 202, cells are seeded within a scaffold. A scaffold may take the form of films/membranes, fibers, fibrous sponges, porous sponges, or hydrogels. The dimensions of the scaffold may be tuned to match the infiltration depth of the specific cell type and scaffold material combination. In some embodiment, to increase (i.e., double) the initial dimensions of the scaffold, cells are seeded on both sides of the scaffold.

In some embodiments, a non-elastic scaffold is compressed to create the target scaffold thickness. In some embodiments, an elastic scaffold is sectioned to the appropriate size to create the target scaffold thickness. In some embodiments, a shape-memory scaffold is used to create the target scaffold thickness.

At 204, a state of a scaffold is modified from a non-extended state to an extended state. When adherent cells proliferate, they grow optimally within a particular density range. The minimum density limit is determined by necessary cell signaling requirements. A maximum density limit is determined by confluency. Due to the phenomenon of contact inhibition, when certain cell types make sufficient direct contact with other cells, they exit the cell cycle and begin to differentiate. Therefore, to encourage and extend the proliferation phase, a state of the scaffold is modified from a non-extended state to an extended state at a rate tuned to keep the cell density within the bounds of the desired density range. In some embodiments, a scaffold is decompressed (non-elastic scaffold) at a rate tuned to keep the cell density within the bounds of the desired density range. In some embodiments, a scaffold is stretched (elastic scaffold) at a rate to keep the cell density within the bounds of the desired range. Growth medium (e.g., cell culture media) is provided to the scaffold while the scaffold is being decompressed or stretched. Expanding the scaffold will continuously increase the surface area available to the cells, inhibiting contact inhibition and enabling a longer proliferation phase while maintaining the minimum cell density necessary to maintain optimal growth.

In some embodiments, the scaffold is continuously expanded from the non-extended state to the extended state. In some embodiments, the scaffold is expanded from the non-extended state to the extended state in a stepwise manner. The expansion may be reversible or cyclical.

At 206, cell differentiation is induced. After a maximum cell density is achieved during the cell proliferation phase, cell differentiation is induced by introducing an alternate culture medium formulation to the scaffold and/or mechanical, electrical, or chemical stimuli. For example, differentiation of myogenic precursor cells may be induced by gradually transitioning media supplemented with a certain concentration of a set of growth factors to a disparate media source, supplemented with a different concentration of a different set of growth factors.

Process 200 can also be applied to non-adherent cells that are encapsulated within a matrix. In this case, the initial phase will see an even distribution of cells throughout the matrix and the scaffold expansion phase will enable increasing volume for non-adherent cells to occupy as they proliferate or differentiate.

Figure 3:
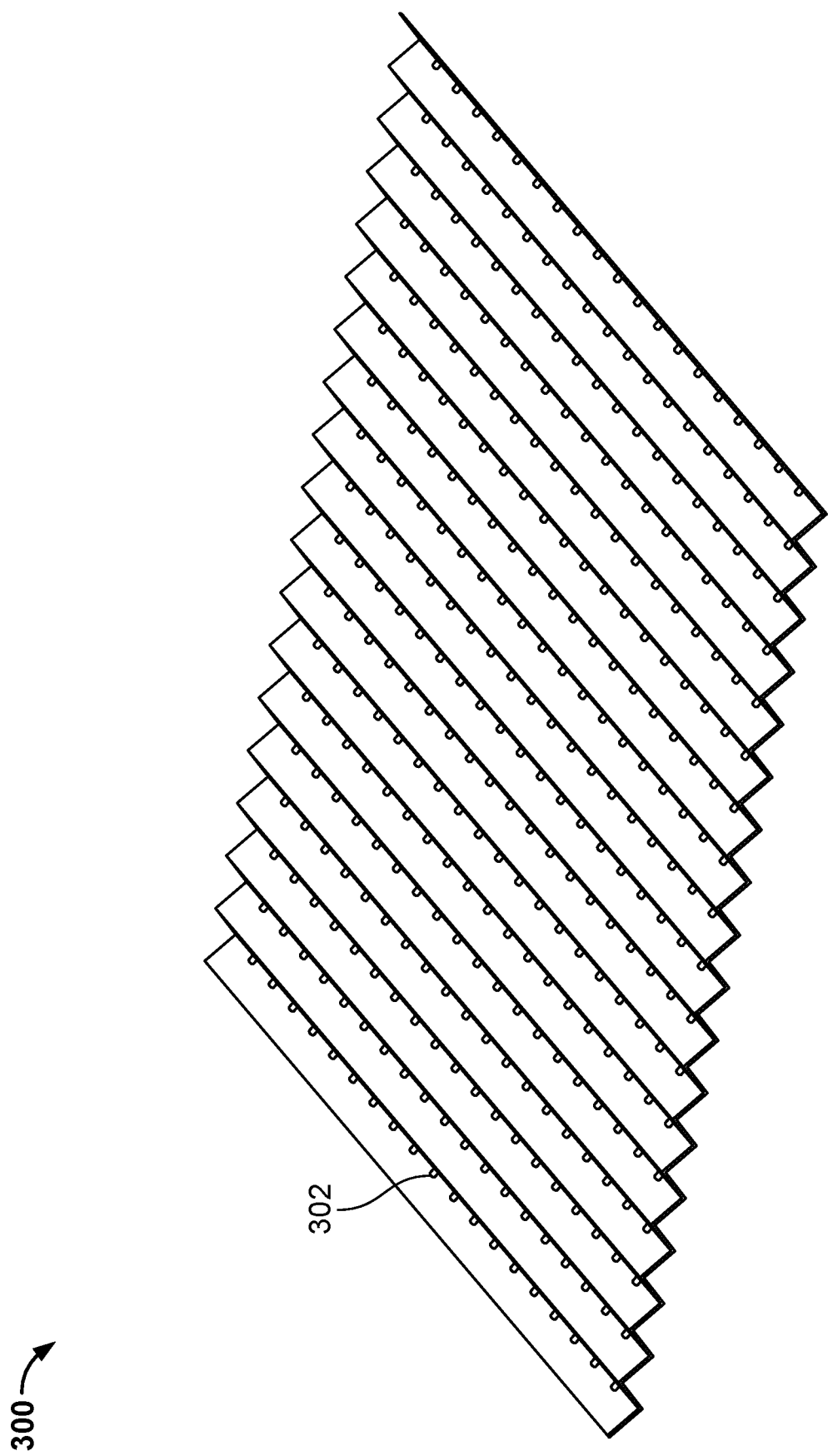
FIG. 3 is a diagram illustrating a scaffold in accordance with some embodiments.
Figure 4A:
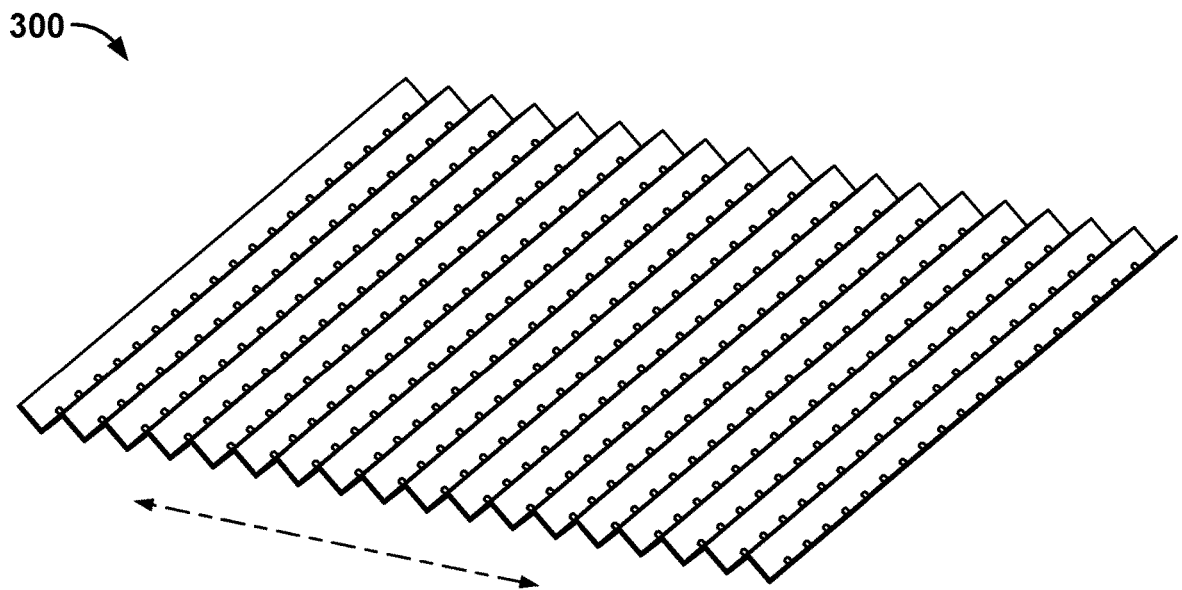
FIGS. 4A and 4B are diagrams illustrating a scaffold being stretched to facilitate cell growth in accordance with some embodiments.
Figure 4B:
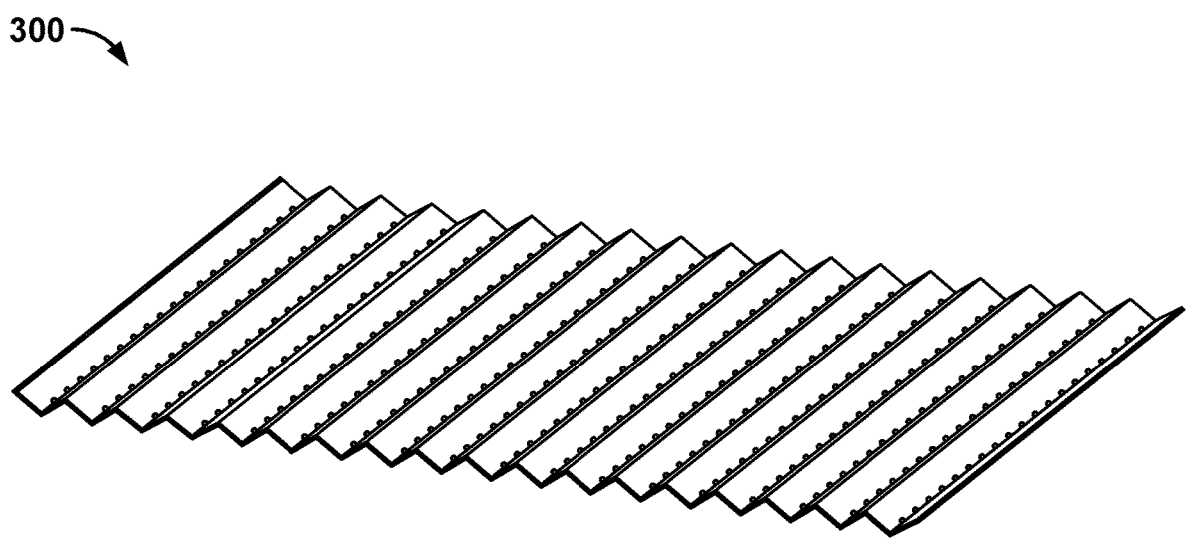

FIG. 3 is a diagram illustrating a scaffold in accordance with some embodiments. In the example shown, scaffold 300 was a flat sheet scaffold that was molded into a zig-zag shape (i.e., a skew apeirogon shape) and perforated with a plurality of holes, such as hole 302 located at bottom valley of the zig-zag shape. The plurality of holes may be generated utilizing a laser, a hole punching template, or other type of hole generating mechanism. Utilizing the zig-zag scaffold may generate a thicker end product when compared to a flat scaffold. In addition, the zig-zag scaffold may be stretched more than a flat scaffold, resulting in an end product having a larger area. FIGS. 4A and 4B illustrate scaffold 300 being stretched to facilitate cell growth to a desired morphology in accordance with some embodiments.

Figure 5:
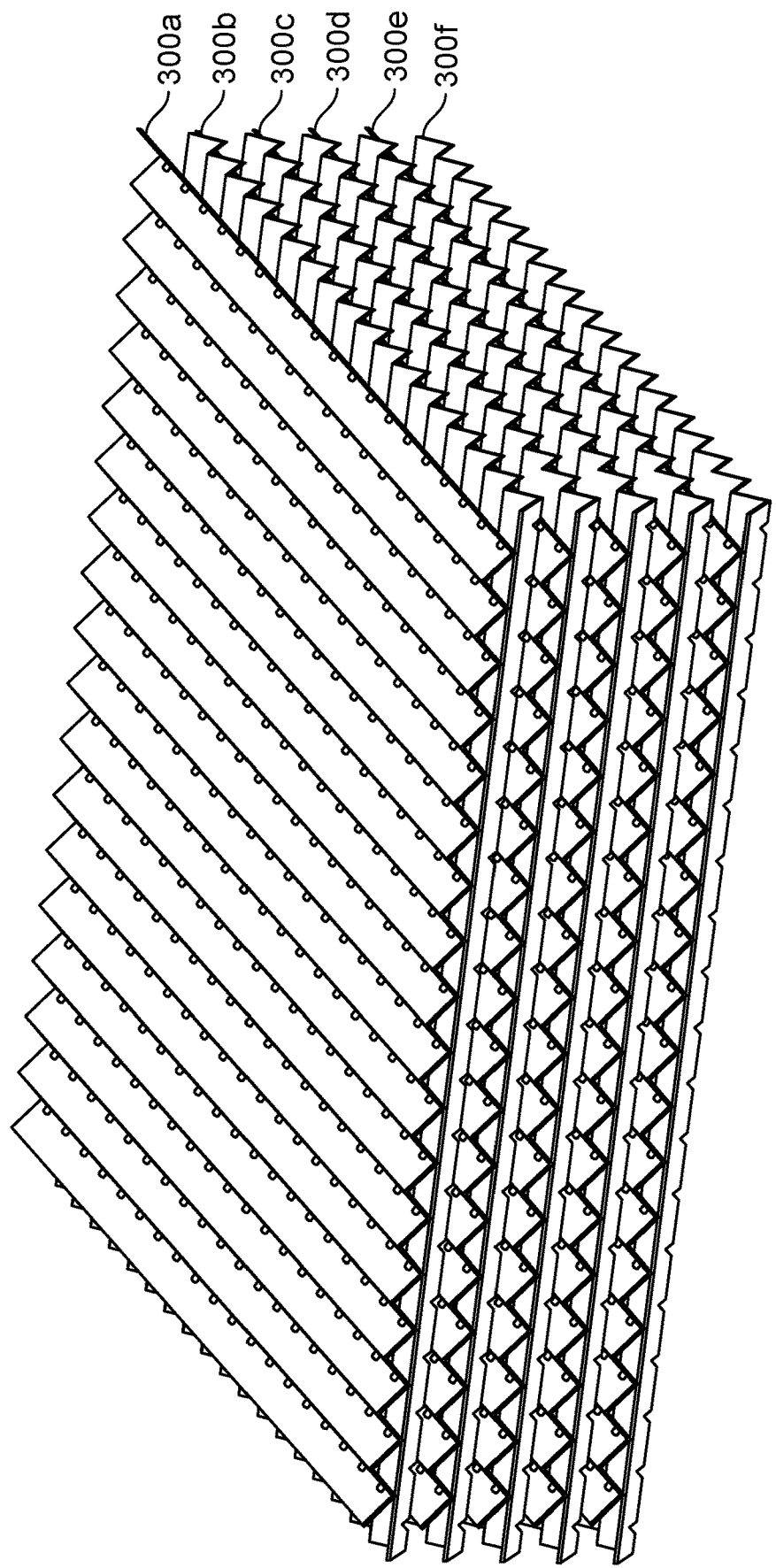
FIG. 5 is a diagram illustrating a plurality of stacked scaffold sheets in accordance with some embodiments.

FIG. 5 is a diagram illustrating a plurality of stacked scaffold sheets in accordance with some embodiments. In the example shown, scaffolds 300*a*, 300*b*, 300*c*, 300*d*, 300*e*, 300*f* are stacked to form an end product having a particular thickness. Although FIG. 5 depicts an end product being generated using six scaffolds, an end product may be generated using n scaffolds. The folded and stacked scaffold sheets 300*a*, 300*b*, 300*c*, 300*d*, 300*e*, 300*f* make it possible to grow muscle cells into a thick-cut at a thickness of choice. Nutrients and oxygen may penetrate deep into the center of the stacked scaffold, thus overcoming the main limitation of conventional sheet scaffold.

FIG. 6A is a diagram illustrating a scaffold support in a vessel in accordance with some embodiments. In the example shown, scaffold 606 has a zig-zag shape and is included in vessel 602. In some embodiments, vessel 602 is a bioreactor. In some embodiments, vessel 602 is a fermenter. A first end of scaffold 606 is attached to floatation device 604*a*. A second end of scaffold 606 is attached to floatation 604*b*. Floatation device 604*a* and floatation device 604*b* are configured to float on liquids included in vessel 602. Floatation devices 608*a*, 608*b* are floating at respective liquid levels 608*a*, 608*b*. As seen in FIG. 6B, the liquid levels 608*a*, 608*b* may be modified to 658*a*, 658*b*, respectively, by draining liquid from vessel 602. As a result, scaffold 606 is stretched from a first position to a second position. The liquid may be drained from vessel 602 at a rate that causes cells to grow on scaffold 606 within an optimal density range. In some embodiments, scaffold 606 may be unstretched by adding liquid to vessel 602.

Figure 7A:
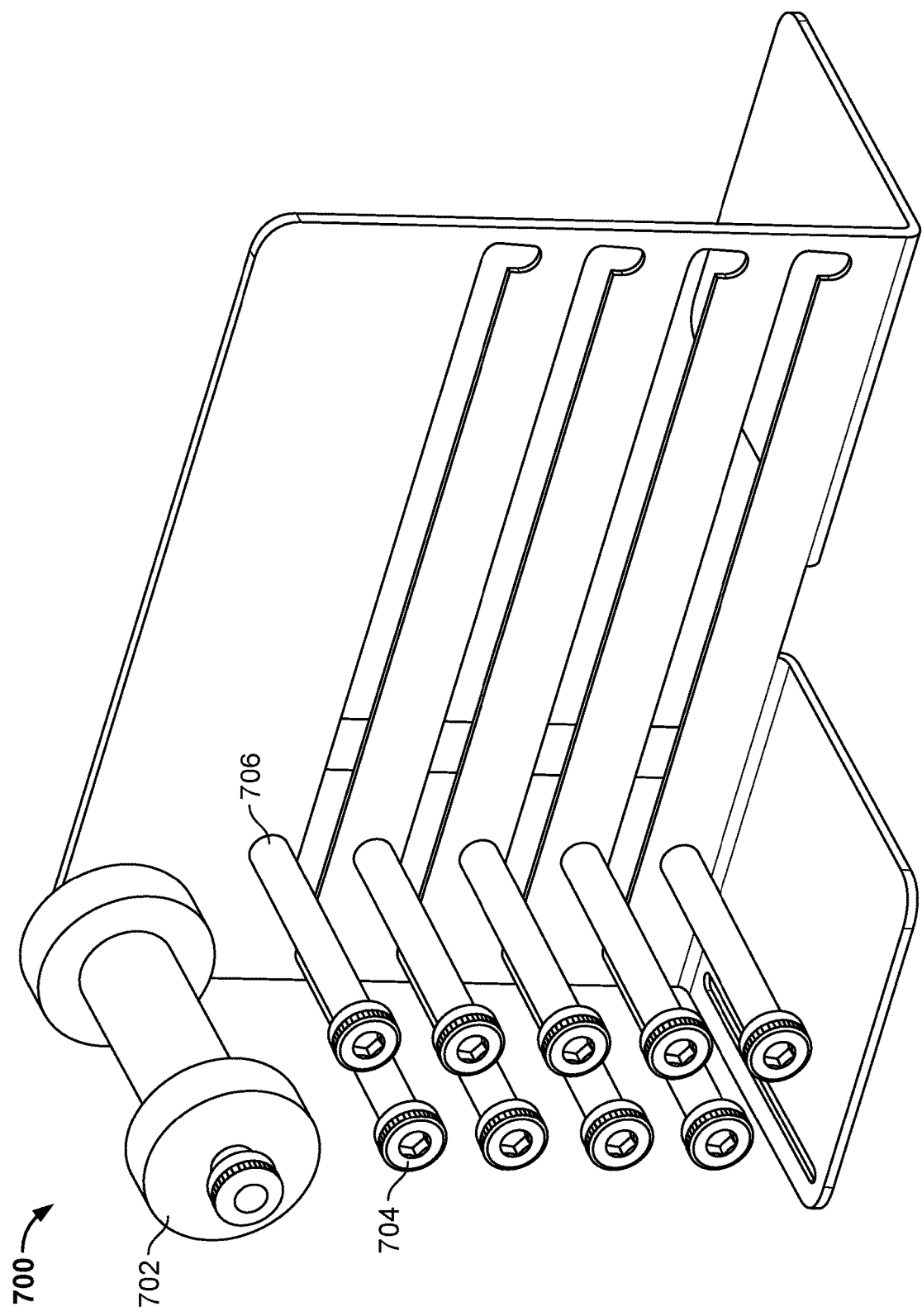
FIG. 7A is a diagram illustrating a scaffold support in accordance with some embodiments.
Figure 7B:
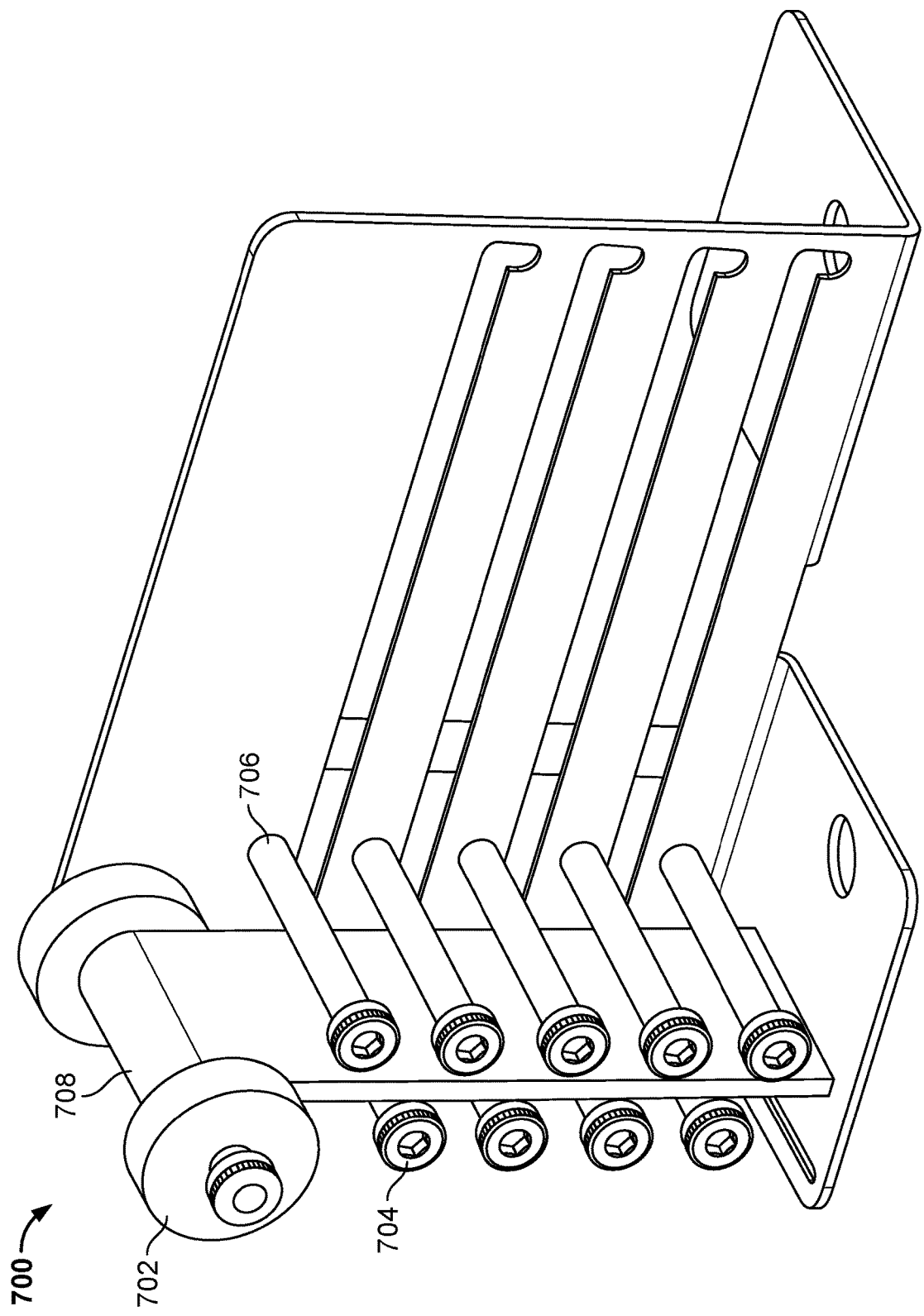
FIG. 7B is a diagram illustrating a scaffold support in accordance with some embodiments.
Figure 7C:
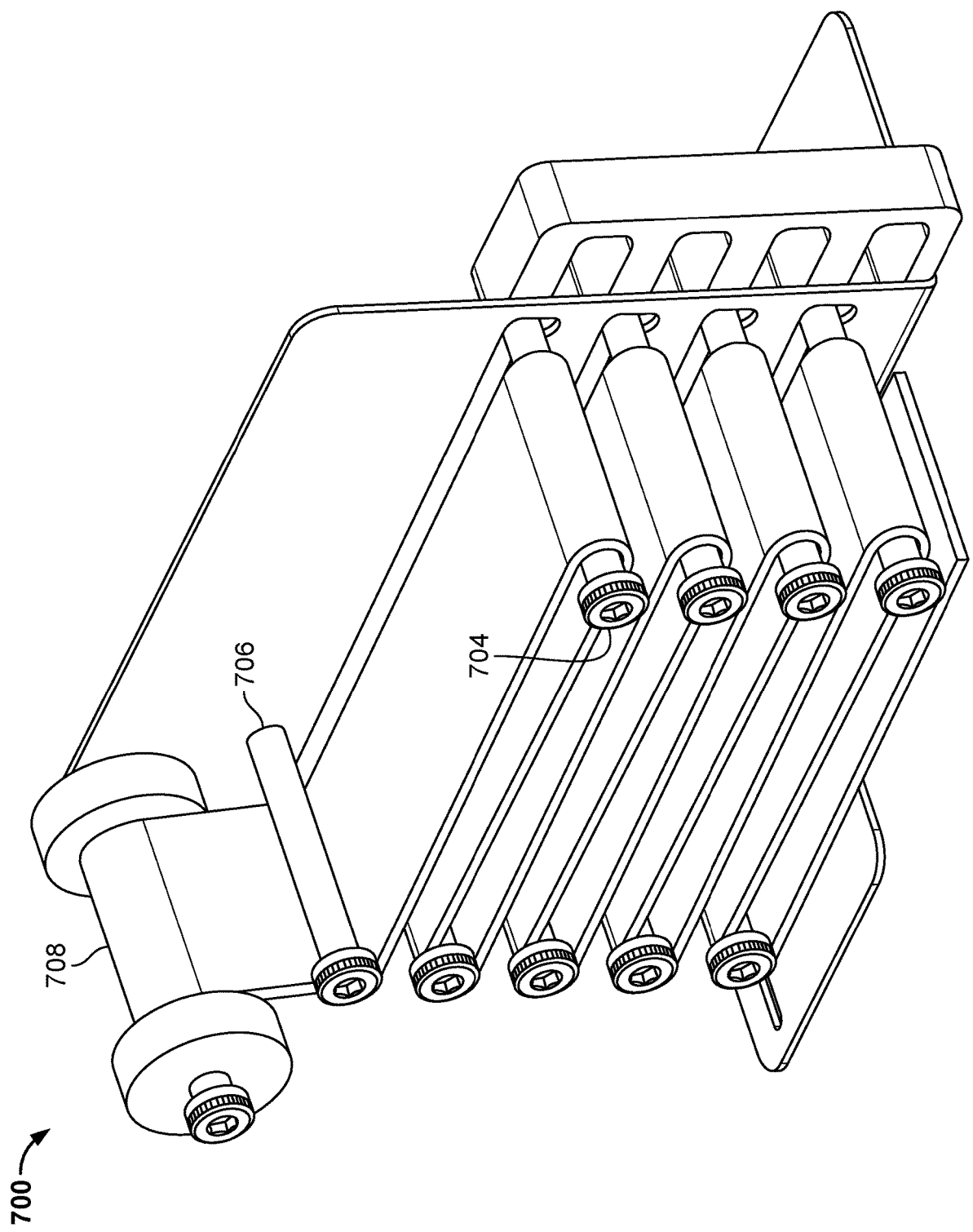
FIG. 7C is a diagram illustrating a scaffold support in accordance with some embodiments.

FIG. 7A is a diagram illustrating a scaffold support in accordance with some embodiments. In the example shown, scaffold support 700 includes a spool 702 and a plurality of rods, such as rods 704, 706. In some embodiments, a scaffold 708 may be wrapped around spool 702 and placed between the plurality of rods, for example as seen in FIG. 7B. Scaffold support 700 may cause scaffold 708 to be modified from a non-extended state to an extended state by adjusting a position of some of the rods. As seen in FIGS. 7B and 7C, a position of rod 704 has been modified from a first position to a second position while a position of rod 706 has not changed. The position of the rods may be adjusted by a mechanical actuator. The mechanical actuator may be an electric motor, a hydraulic cylinder, a pneumatic actuator, a linear actuator, a piezoelectric actuator, a rack and pinion mechanism, a rotary solenoid, etc. The mechanical actuator may be coupled to a processor. The processor may cause the actuator to adjust the position of the rods such that scaffold 708 is adjusted at a rate that causes cells to grow within an optimal density range.

Figure 8:
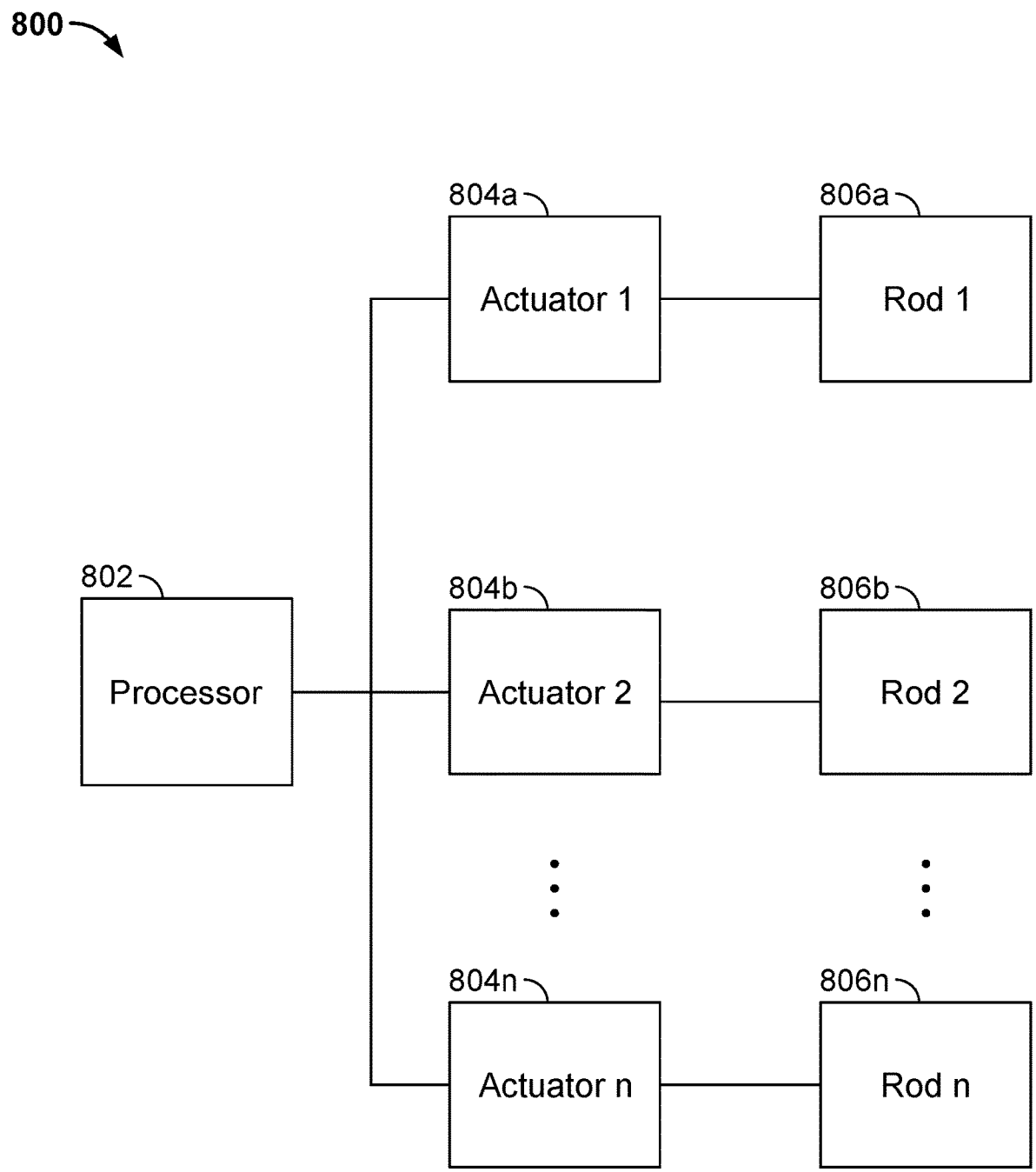
FIG. 8 is a block diagram illustrating a control system for a scaffold support in accordance with some embodiments.

FIG. 8 is a block diagram illustrating a control system for a scaffold support in accordance with some embodiments. In the example shown, system 800 includes processor 802 coupled to actuators 804*a*, 804*b*, . . . , 804*n*. Although FIG. 8 depicts processor 802 being coupled to three actuators, processor 802 may be coupled to n actuators. Each of the actuators 804*a*, 804*b*, . . . , 804*n* is coupled to a corresponding rod 806*a*, 806*b*, . . . , 806*n*. Processor 802 may send a control signal to an actuator that causes the actuator to change a position of a corresponding rod from a first position to a second position. Processor 802 may send a control signal to an actuator that causes the actuator to change a position of a corresponding rod from the second position to the first position. Processor 802 may send a control signal to an actuator that causes the actuator to change the position of its corresponding rod at a particular rate. The particular rate may correspond to a rate that causes cells to grow within a scaffold at an optimal density range.

Figure 9B:
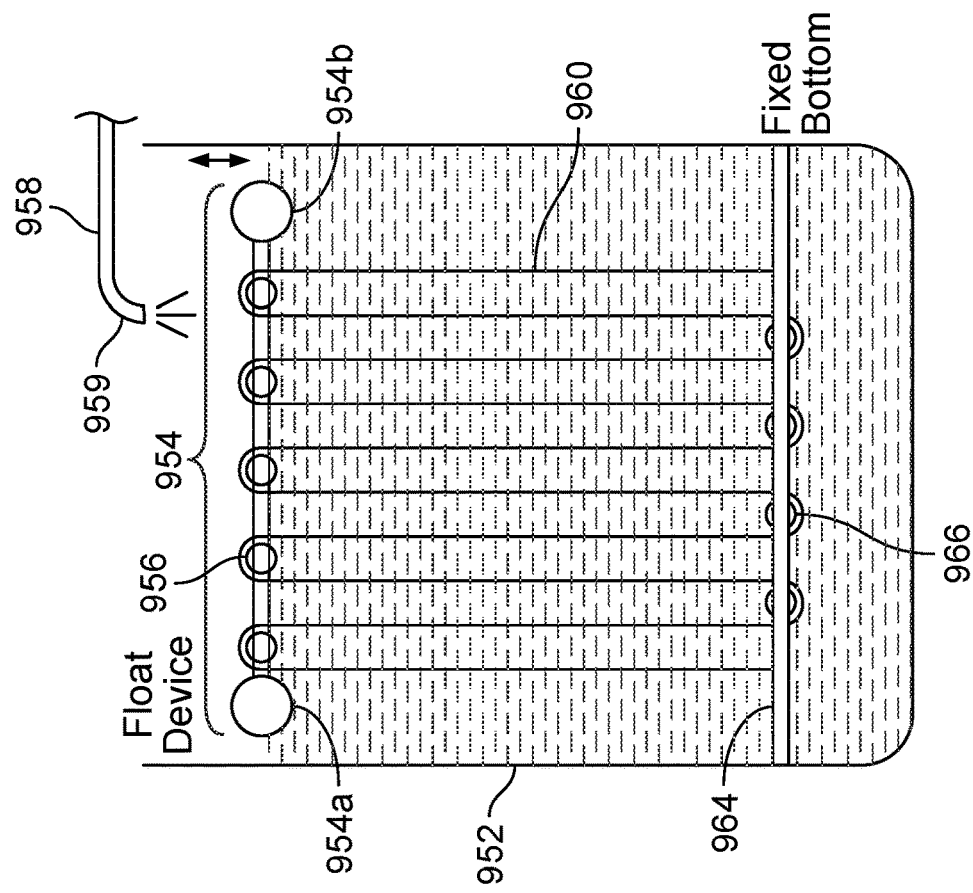
FIG. 9B is a diagram illustrating a buoyancy driven scaffold support in accordance with some embodiments.
Figure 9A:
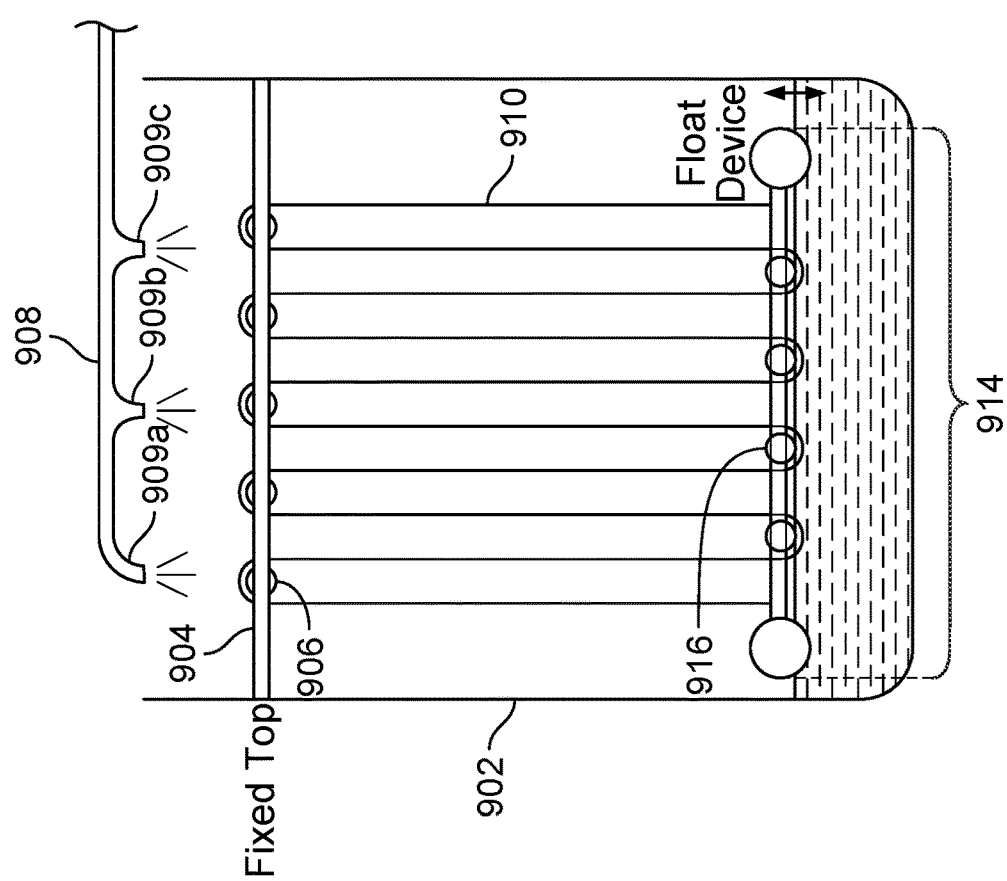
FIG. 9A is a diagram illustrating a buoyancy driven scaffold support in accordance with some embodiments.

FIG. 9A is a diagram illustrating a buoyancy driven scaffold support in accordance with some embodiments. In the example shown, the buoyancy driven scaffold support includes a fixed top portion 904 that is coupled to the sides of vessel 902. In some embodiments, vessel 902 is part of a bioreactor. In some embodiments, vessel 902 is part of a fermenter. The fixed top portion 904 includes a plurality of rods, such as rod 906. The bottom portion of the buoyancy driven scaffold stretch devices include floatation devices 914 and a plurality of rods, such as rod 916. A scaffold sheet 910 may be wrapped around the plurality of rods. Buoyancy within vessel 902 may be leveraged to control an amount and a rate at which scaffold 910 is stretched and unstretched. By controlling the liquid level in the vessel, the scaffold sheet 910 can be stretched and unstretched. The liquid level within vessel 902 may be controlled by a media feed and drain rate. Gravity may assist in modifying a state of the scaffold sheet 910 from the stretched and unstretched states.

A fluid, such as growth media or differentiation media, is provided to the scaffold sheet 910 via manifold 908 that includes dispensers 909*a*, 909*b*, 909*c*. Although FIG. 9A depicts manifold 908 having three dispensers, manifold 908 may include 1:n dispensers.

FIG. 9B is a diagram illustrating a buoyancy driven scaffold support in accordance with some embodiments. In the example shown, the buoyancy driven scaffold support includes a fixed bottom portion 964 that is coupled to the sides of vessel 952. In some embodiments, vessel 952 is part of a bioreactor. In some embodiments, vessel 952 is part of a fermenter. The fixed bottom portion 964 includes a plurality of rods, such as rod 966. The top portion of the buoyancy driven scaffold support includes floatation device 954 and a plurality of rods, such as rod 956. A scaffold sheet 960 may be wrapped around the plurality of rods. Buoyancy within vessel 952 may be leveraged to control an amount and a rate at which scaffold 960 is stretched and unstretched. By controlling the liquid level in the vessel, the scaffold sheet 960 can be stretched and unstretched. The liquid level within vessel 952 may be controlled by a media feed and drain rate. Gravity may assist in modifying a state of the scaffold sheet 910 from the stretched and unstretched states.

A fluid, such as grown media or differentiation media, is provided to the scaffold sheet 960 via manifold 958 that includes dispenser 959. Although FIG. 9B depicts manifold 958 having one dispenser, manifold 958 may include 1:n dispensers.

FIGS. 10A and 10B are diagrams illustrating a scaffold support in accordance with some embodiments. In the example shown, the scaffold support 1000 includes a first side 1006*a* and a second side 1006*b*. The first side 1006*a* and the second side 1006*b* are coupled to each other via a first rod 1008 and a second rod 1010. The first side 1006*a* includes an opening 1012*a* and the second side 1006*b* includes an opening 1012*b*. As seen in FIGS. 10A and 10B, the first rod 1008 is capable moving from a first position on the openings 1012a, 1012b to a second position on the openings 1012a, 1012b and from the second position on the openings 1012a, 1012b to the first position on the openings 101a, 1012b.

A scaffold 1004 is secured by a first hanger clamp 1002a and a second hanger clamp 1002b. The first rod 1008 is coupled to the first hanger clamp 1002a and the second rod 1010 is coupled to the second hanger clamp 1002b. A state of the scaffold changes from a non-extended state as seen in FIG. 10A to an extended state as seen in FIG. 10B when the first rod 1008 moves from the first position to the second position. The state of the scaffold may return from the extended state as seen in FIG. 10B to the non-extended state as seen in FIG. 10A.

Gravity may assist in changing the state of the scaffold from the non-extended state to the extended state. In some embodiments, actuators (not shown) are coupled to the ends of the first rod 1008 and cause the first rod to move from the first position on the openings 1012a, 1012b to the second position on the openings 1012a, 1012b.

Figure 11:
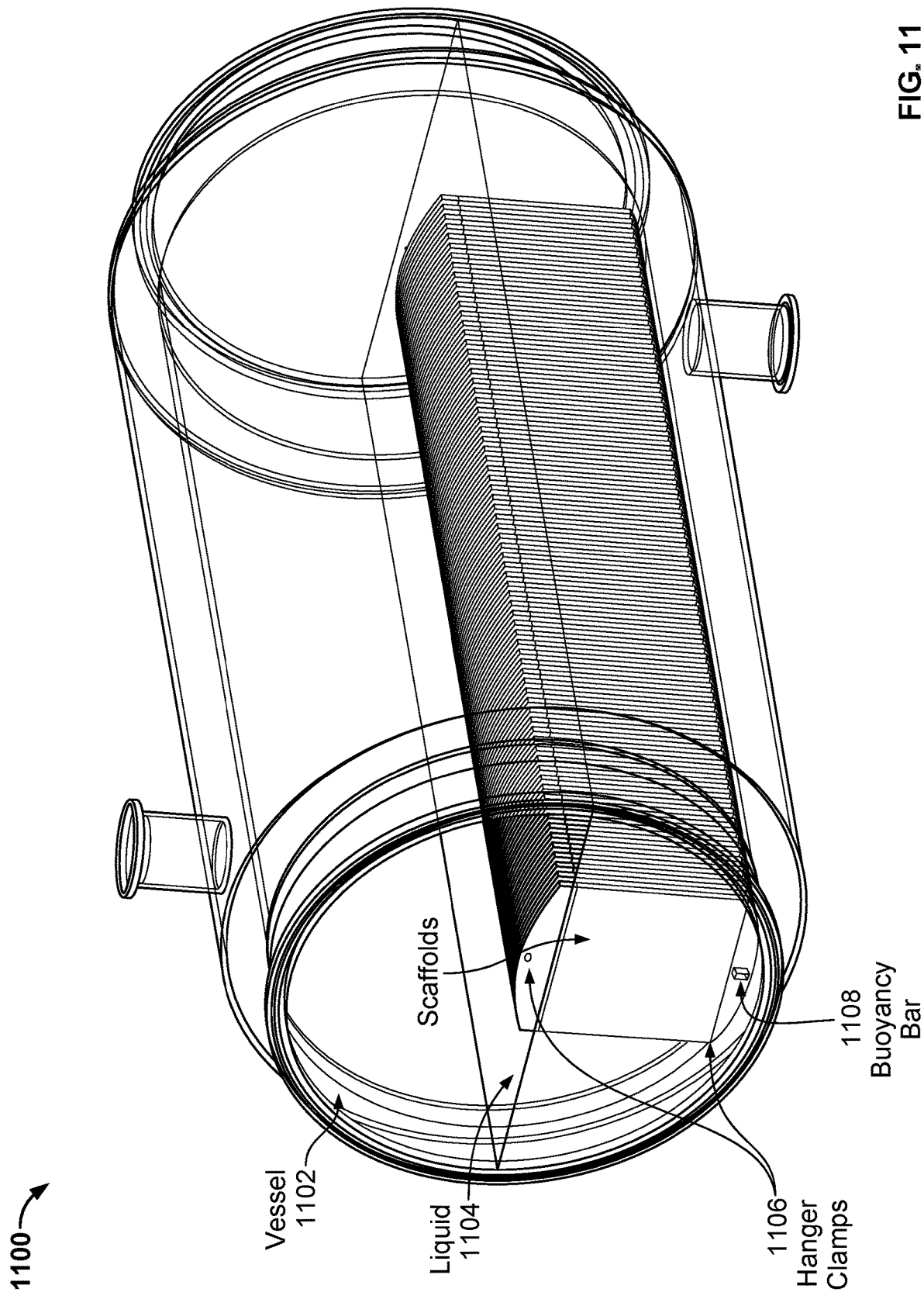
FIG. 11 is a diagram illustrating a scaffold support in accordance with some embodiments.

FIG. 11 is a diagram illustrating a scaffold support in accordance with some embodiments. FIG. 11 depicts the scaffold support 1100 positioned within a vessel 1102. The vessel 1102 includes a liquid (e.g., media) 1104. The scaffold support 1100 includes a plurality of hanger clamps 1106, each pair of hanger clamps being associated with a corresponding scaffold. Scaffold support 1100 includes a buoyancy bar 1108 positioned through the bottom hanger clamps of the plurality of hanger clamps 1106. The buoyancy bar 1108 enables the scaffold support 1100 to float in the liquid 1104. The plurality of scaffolds may change from a non-extended state to an extended state or from the extended state to the non-extended state based on a liquid level of liquid 1104 within vessel 1102.

EXAMPLES

Example 1. Case Study—Determining the Target Stretch Rate of an Elastic Scaffold A thin, flat scaffold is initially 1 cm long and 25 cm wide (initial size) and can be plastically deformed via stretching to 4 cm long (final size) without fracture and without compromising width. For the target cell type, the minimum seeding density is 2,000 cells/cm2 and the maximum confluent density is 100,000 cells/cm2. The cell doubling time is 24 hours.

Scenario A. Scaffold is seeded and cultured at initial size. The scaffold is seeded at 2,000 cells/cm2 which requires 50,000 cells for the 25 cm2 initial size scaffold. The maximum density is reached after 135 hours (~6 days) in culture. The final product required an input of cells, is 25 cm2 and contains a total of 2.5 M cells.

Scenario B. Scaffold is stretched, then seeded and cultured at final size. The scaffold is seeded at 2,000 cells/cm2 which requires 200,000 cells for the 100 cm2 initial size scaffold. The maximum density is reached after 135 hours (~6 days) in culture. The final product required an input of 200,000 cells, is 100 cm2 and contains a total of 10 M cells.

Scenario C. Scaffold is seeded at initial size and stretched to final size during culture. The scaffold is seeded at 2,000 cells/cm2 which requires 50,000 cells for the 25 cm2 initial size scaffold. The scaffold is stretched from 1 cm to 4 cm length over the course of 183 hours (~8 days) which corresponds to a rate of 0.16 mm/hour. The final product required an input of 50,000 cells, is 100 cm2 and contains a total of 10 M cells.

Example 2. Origami Approach to Grow Thick-Cut Meat

A flat sheet of scaffold material limits how thick a whole-cut meat one can grow. To overcome this limitation, scaffold sheets could be folded (FIG. 3) and stacked (FIG. 5).

To further facilitate the mass transfer of nutrients and oxygen into the scaffold layers, the folded scaffold is perforated in the grooves. Cell culture media introduced to the upper layers can sequentially percolate through the entire structure. As a result, the interior of the scaffold structure also receives adequate nutrients and oxygen. In addition, the metabolic waste will be carried away by media drained from the bottom.

Example 3. Woven Scaffold Support

Thin, flat sponges or fibrous membrane biomaterials are promising scaffold candidates for cultivated meat production because they are easy to manufacture, can recapitulate the extracellular matrix, and do not require cells to migrate far from the surface of seeding. There is no current standard for culturing cells on membrane scaffolds in a scalable bioreactor. One challenge is maximizing the surface area of the scaffold while enabling nutrient and oxygen transfer. Therefore, there is a need for a bioreactor system that couples membrane-based scaffolds within a bioreactor system while maximizing surface area. One concept to address this problem is a device (FIG. 7A) that can transform a membrane scaffold into a multi-layered format while facilitating media transfer between layers and providing passive tension to support unidirectional cell alignment.

First, a prefabricated membrane scaffold is wound around a spool. The dimensions of the scaffold (width, length) can be dictated by the desired dimensions of the end-product and the thickness of scaffolds can be dictated by the infiltration depth of the cell type of interest. The scaffold can be unwound, threaded between the rods of the device, and clamped to secure. The outer set of rods can be moved to the other side of the device as the scaffold further unwinds to create multiple layers with predetermined spacing. This approach enhances the surface area of the scaffold within a bioreactor and provides passive tension to the material and adhered cells. During culture, the rods can be moved to stretch, relax, and or compress the scaffold at predetermined rates and times.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A bioreactor, comprising:
   a scaffold seeded with a plurality of cells and having an extended state and a non-extended state;
   a scaffold support that selectively modifies a state of the scaffold from the non-extended state to the extended state; and
   a manifold configured to provide a medium to the scaffold, wherein the scaffold support modifies the state of the scaffold from the non-extended state to the extended state at a rate tuned to maintain a cell density associated with the plurality of cells within a particular density range.

2. The bioreactor of claim 1, wherein the scaffold is a non-elastic scaffold.

3. The bioreactor of claim 2, wherein the scaffold support is configured to decompress the scaffold from the non-extended state to the extended state.

4. The bioreactor of claim 1, wherein the scaffold is an elastic scaffold.

5. The bioreactor of claim 4, wherein the scaffold support is configured to stretch the scaffold from the non-extended state to the extended state.

6. The bioreactor of claim 1, wherein the scaffold is a shape-memory scaffold.

7. The bioreactor of claim 1, wherein the scaffold has a skew apeirogon shape.

8. The bioreactor of claim 7, wherein the scaffold has a plurality of holes located at valleys of the scaffold.

9. The bioreactor of claim 7, wherein the scaffold is stacked on top of one or more other scaffolds having the skew apeirogon shape.

10. The bioreactor of claim 7, further comprising:
a first liquid region and a second liquid region that is different than the first liquid region, wherein the scaffold support includes a first floatation device attached to a first end of the scaffold and a second floatation device attached to a second end of the scaffold, wherein the first floatation device is floating in the first liquid region and the second floatation device is floating in the second liquid region.

11. The bioreactor of claim 10, wherein the state of the scaffold is modified from the non-extended state to the extended state or from the extended state to the non-extended state by controlling a liquid level associated with the bioreactor.

12. The bioreactor of claim 1, wherein the scaffold support includes a spool, a first set of rods and a second set of rods.

13. The bioreactor of claim 12, wherein in the non-extended state, the scaffold is wrapped around the spool and placed between the first set of rods and the second set of rods.

14. The bioreactor of claim 13, wherein the first set of rods are coupled to a set of actuators.

15. The bioreactor of claim 14, wherein to modify the state of the scaffold from the non-extended state to the extended state, a processor provides a control signal to the set of actuators that causes the first set of rods to move from a first position to a second position, wherein in the extended state, the scaffold is alternately woven between the first set of rods and the second set of rods.

16. The bioreactor of claim 15, wherein the first set of rods move from the first position to the second position at the rate tuned to maintain the cell density associated with the plurality of cells within the particular density range.

17. The bioreactor of claim 12, wherein the first set of rods are located at a fixed location of the bioreactor and the second set of rods are coupled to a floatation device located within the bioreactor.

18. The bioreactor of claim 17, wherein the state of the scaffold is modified from the non-extended state to the extended state or from the extended state to the non-extended state by controlling a liquid level associated with the bioreactor.

19. The bioreactor of claim 1, wherein the medium is growth medium.

20. The bioreactor of claim 1, wherein the medium is differentiation medium.

21. The bioreactor of claim 1, wherein after a particular cell density is achieved for the plurality of cells, differentiation is induced in the plurality of cells by introducing a differentiation medium via the manifold.

22. The bioreactor of claim 1, wherein after a particular cell density is achieved for the plurality of cells, differentiation is induced in the plurality of cells by mechanical, electrical, or chemical stimuli.

23. The bioreactor of claim 1, wherein the manifold is configured to provide the medium to the scaffold while the scaffold is being modified from the non-extended state to the extended state.

* * * * *